US005690099A

United States Patent [19]

Abramov et al.

[11] Patent Number: 5,690,099

[45] Date of Patent: Nov. 25, 1997

[54] METHOD AND APPARATUS FOR REVITALIZING EXHALED AIR

[75] Inventors: Vladimir Victorovich Abramov, Moscow, Russian Federation; Robert M. Hamilton, Brea, Calif.

[73] Assignee: Life Support Technologies, Inc., Pensacola, Fla.

[21] Appl. No.: 681,126

[22] Filed: Jul. 22, 1996

[51] Int. Cl.[6] .................... A61M 15/00

[52] U.S. Cl. .................... 128/202.26; 128/205.12

[58] Field of Search .................... 128/202.26, 205.12, 128/205.13, 205.17, 205.22, 205.28, 205.21

[56] References Cited

U.S. PATENT DOCUMENTS 5,036,841 8/1991 Hamilton .

OTHER PUBLICATIONS

Air Revitalization Compounds: a Literature Study—published in the test Toxicological and Environmental Chemistry 1985, vol. 10, pp. 133–155 by Messrs. J.O. Stull and M.G. While.

Computer printout of abstracts of articles and/or patent applications noted in a computer search—applicants' attorney has not obtained copies of the actual articles or applications.

*Primary Examiner*—Vincent Millin
*Assistant Examiner*—Robert N. Wieland
*Attorney, Agent, or Firm*—Harold L. Jackson

[57] ABSTRACT

A canister containing one or more working compounds formed of a peroxide and/or superoxide of one or more metals of the alkali and alkaline-earth metal groups such as $KO_2$ and $CaO_2$ and a moisture releasing material such as wetted activated charcoal is utilized to replenish the oxygen and absorb the carbon dioxide in exhaled air. The canister may be used in a closed or semi-closed circuit breathing system worm by a user such as a fireman, miner etc.

33 Claims, 8 Drawing Sheets

METHOD AND APPARATUS FOR REVITALIZING EXHALED AIR

FIELD OF THE INVENTION

The present invention relates to a method and apparatus for revitalizing air which has passed through a person's lungs (i.e., exhaled air) to increase the oxygen ($O_2$) and reduce the carbon dioxide ($CO_2$) content thereof so that the air is again life supporting.

DESCRIPTION OF THE PRIOR ART

It is well known that certain peroxides and superoxides of the alkali and alkaline earth metals absorb carbon dioxide and produce oxygen. Of these, lithium peroxide (LiO), calcium peroxide ($CaO_2$), potassium superoxide ($KO_2$), and sodium superoxide ($NaO_2$) appear to be the most practical from the availability standpoint and the latter three would seem to be the most practical from the standpoint of cost. See the article by Messrs. J. O. Stull and M. G. While entitled *Air Revitalization Compounds: a Literature Study* published in the text *Toxicological and Environmental Chemistry* 1985, Vol. 10, pp. 133–155.

A major obstacle to the use of such compounds in emergency breathing systems, for example of the closed-circuit type, where exhaled air is to be rebreathed, is the generation of heat. The temperature of the gas in the reaction zone of the compounds will be of the order of several hundred degrees fahrenheit. Rejection of the heat may not be a problem in space or underwater applications. However, the temperature of the air revitalized by passing through such compounds is a major drawback to the use of such compounds in other environments. Closed-circuit emergency breathing systems employing $KO_2$, as the revitalizing reagent, have been used in mine rescue operations for many years. The successful use of such systems has been dependent, to a large extent, on training the rescue workers to tolerate the high temperature of the recirculating gas, which may approach or even be in excess of 110° F. as inhaled by the worker. In addition to the temperature problem, there is an initial time delay of several minutes or more before such air revitalization compounds commence generating appreciable amounts of oxygen. It is believed that this delay is due to the requirement of water for the chemical reaction to take place with moisture being gradually provided as a component of the exhaled air from the user, e.g, rescue worker or patient.

There is a need for a method and apparatus for revitalizing exhaled air which overcomes the above problems.

SUMMARY OF THE INVENTION

In accordance with the method aspect of the present invention, exhaled air from person is passed through a bed of a working compound of a peroxide and/or superoxide of one or more metals of the groups consisting of the alkali and alkaline-earth metals, such as $KO_2$, $NaO_2$, and $CaO_2$. The air is then passed through a bed of a moisture releasing material such as wetted activated charcoal to reduce the temperature thereof and accelerate the $O_2$ generating activity of the working compound. Where a system is needed for a substantial time period, such as 1–2 hours for fighting fires etc., air from a pressurized container, for example, may be added to revitalize air circulating in the system. Such a system is generally referred to as semi-closed circuit systems because air is being added to the exhaled air from the user.

In accordance with the apparatus of the present invention, a container, in the form, for example, of a canister, is provided with an inlet for receiving exhaled air having an excess $CO_2$ and a diminished $O_2$ content and an outlet through which the revitalized air passes. A first bed containing a working compound of a peroxide and/or superoxide of one or more metals of the alkali and alkaline-earth metals (such as $KO_2$, $NaO_2$, and $CaO_2$) is disposed within the canister to contact the air as it flows from the inlet to the outlet and a second bed containing a moisturizing material is located in the canister downstream from the working compound. Preferably the moisturizing material is wetted activated charcoal containing sufficient moisture to maintain the temperature of the outlet air at about 100° F., and preferably less, for the designed life of the apparatus, such as 20–30 minutes for short term emergency applications and 2 or more hours for longer term applications.

To provide an acceptable shelf life for the apparatus, the working compound and the moisturizing material may be separately encapsulated in impermeable membranes which membranes may be ruptured immediately prior to use. Also a third bed of dry activated charcoal may be placed downstream of the bed of wetted charcoal to reduce the humidity of the outlet air.

A canister loaded with the air revitalizing compound may be disposed within a rebreather bag secured to the user's body to provide a closed-circuit breathing system. Suitable inhalation and exhalation valves may be arranged to pass the exhaled air through the canister before such air is inhaled. Again, it should be noted that for long term applications it may be desirable to add external air to the system via a pressurized container.

The features of the present invention may be best understood by reference to the following description of the preferred embodiment taken in conjunction with the accompanying drawings.

DESCRIPTION OF THE PREFERRED EMBODIMENTS

Figure 1:
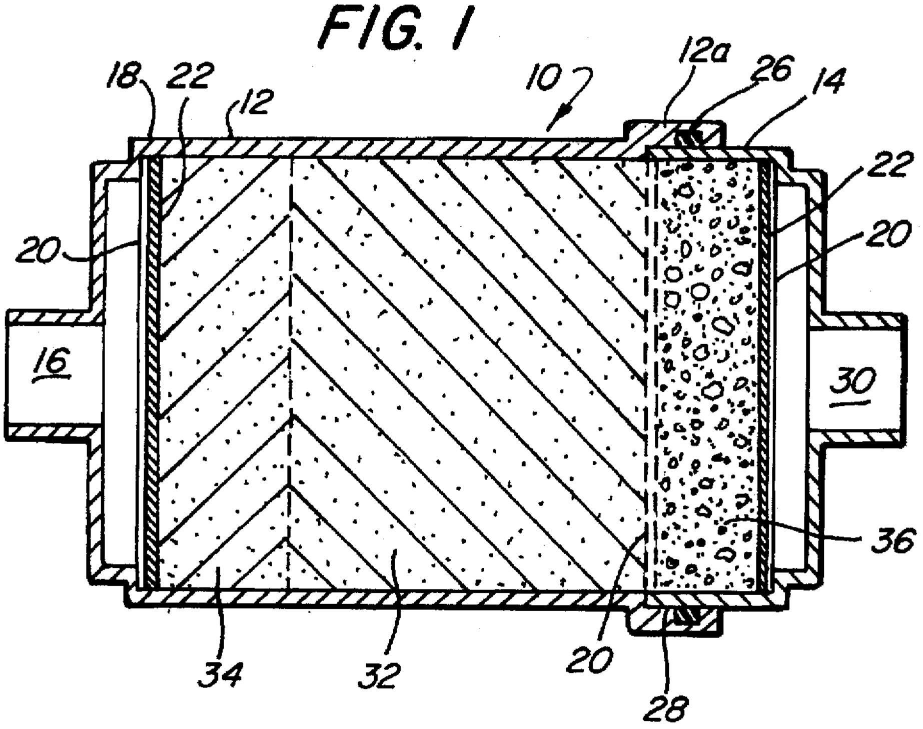
FIG. 1 is a cross-sectional view of a canister containing air revitalizing compounds in accordance with the invention.

Referring now to FIG. 1, a cylindrical canister or container 10, for containing the air revitalizing compounds of the present invention, includes a front section 12 and a detachable rear section 14. The front section 12 is formed with an air inlet opening 16 and an inwardly projecting shoulder 18 which forms a seat for a metal or fiberglass screen 20 and a dust filter 22 (which also may be made of fiberglass). The front section 12 further includes an annular flange 12*a* provided with a elastomeric o-ring 26, or other suitable gasket material disposed within an inner groove thereof, as illustrated. The rear section 14 of the canister includes a forward portion 28 which is arranged to be seated within the flange 24 so that the O-ring 26 forms a substantially air-tight seal with the outer periphery thereof. The rear section 14 includes an air outlet 30.

The air revitalizing chemicals loaded into the canister 10 comprise one or more compounds formed of a peroxide and/or superoxide of one or more metals of the alkali and alkaline-earth metal groups and a moisturizing material located downstream from the working compound(s). The alkali-metals may include lithium (Li), sodium (Na), potassium (Ka) and perhaps rubidium (Rb) and cesium (Cs), although working compounds incorporating the latter two metals have not been prepared or tested. The alkaline metals may include magnesium (Mg), calcium (Ca), and barium (Ba), although again working compounds incorporating magnesium and barium have not been prepared or tested. A main working compound may be disposed in a bed 32 and a separate auxiliary working compound may be disposed in a bed 34 in the canister.

Preferably the main working compound in bed 32 comprises granules of $KO_2$ and/or $NaO_2$ (and most preferably $KO_2$). Granules of both $KO_2$ and $NaO_2$ have a tendency to form a crust during their chemical reaction with $CO_2$ and $H_2O$, which crust reduces the porosity of the compound and increases the resistance to air flow therethrough. In addition, the formation of crust reduces the surface area of the compound available for further chemical reaction, thereby shortening the time that the working compound is effective in maintaining the air suitable for rebreathing.

We have discovered that granules of $CaO_2$, when added to the granules of $KO_2$ and/or $NaO_2$ aids in alleviating the crusting and porosity problem. Preferably the main working compound comprises $KO_2$ (or $NaO_2$) within a range of about 30 to 70% (and most preferably about 60%) by volume with the remainder of the compound consisting of $CAO_2$. We have also found that a second bed 34 of $CaO_2$ (e.g., an auxiliary working compound) disposed upstream from the main working compound is a further aid in reducing the crusting and porosity problem.

Figure 7:
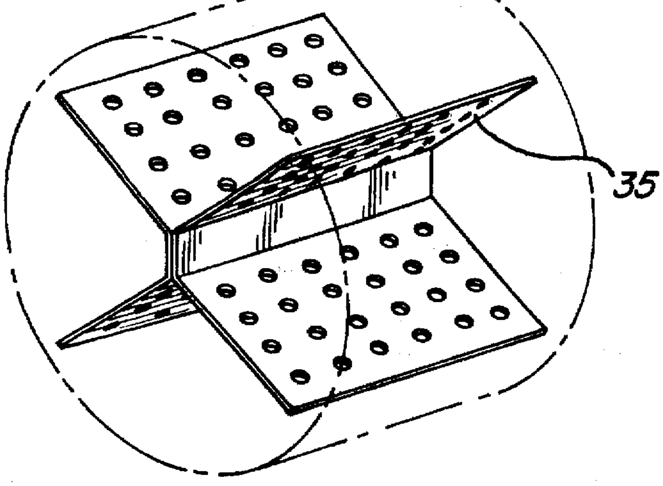
FIG. 7 is a perspective view of a partition that may be inserted into the canisters of FIGS. 1, 2, 5 and 6 to divide the contents thereof into separate quadrants.

It has further been determined that about 200 cm$^3$ of the main working compound, i.e., $KO_2$ and $CaO_2$, in bed 32, will maintain the air in a closed-circuit breathing system suitable for human use for about 20 to 30 minutes. Where a second bed of $CaO_2$ (bed 34) is to be used, the ratio of volume of the main working compound in bed 32 to the volume of the auxiliary working compound in bed 34 may range from about 3:1 to about 9:1, for example. A perforated partition 35, shown in FIG. 7 and made, for example, of metal may be inserted inside the canister shell 12 prior to the placement of the working compounds therein. The partition aids in inhibiting the tendency of the $KO_2$ or $NaO_2$ to cake or crust over while the perforations in the partition promote the circulation of the air (or gas) throughout the working compound bed.

As discussed in the prior art section above, the use of an alkali and/or alkaline-metal peroxide or superoxide to revitalize air has two drawbacks. The output air is hot and the generation of appreciable amounts of $O_2$ is delayed.

It has been discovered that the addition of a moisture-releasing material disposed downstream from the working compound(s) in beds 32 and/or 34, overcomes both drawbacks to a large extent. Such a moisture-releasing material may be in the form of a suitable clay, cotton, paper etc. However, activated charcoal is very effective in cooling the air exiting the working compound(s) through the vaporization of water and activated charcoal has the further advantage in that it absorbs unwanted odors associated with respiration. For this reason, a bed 36 of wetted-activated charcoal is preferably located in the rear section 14 of the canister downstream from the $KO_2CaO_2$ granules in bed 32. The rear section 14 of the canister is designed to be snapped into the front section 12 just prior to use. Both sections of the canister are preferably encased in separate impermeable membranes, such as heat sealed polyethylene, prior to use to prevent moisture from migrating into the working compounds and initiating a unwanted chemical reaction prior to use by personnel.

we have found that 150 cm$^3$ of activated charcoal containing 50 cm$^3$ of distilled water when used in conjunction with the quantity of working compounds discussed above is satisfactory in maintaining the outlet air in the closed circuit breathing system at a temperature at or below an individual's body temperature (98° F.) for the life expectancy of the system and for triggering the early generation of oxygen by the working compound(s).

Metal or fiberglass screens 20 separate the working compound in bed 32 from the charcoal in bed 36. Another dust filter 22 and screen 20 may also be placed between the charcoal bed 36 and the outlet 30.

$KO_2$ and $NaO_2$, in substantially pure form, with 1% or less impurities, are available commercially in granular form. The granules are generally of irregular shape with an average diameter of about 3–6 mm and may be used in that form. $CaO_2$ is generally available as a powder and preferably should be prepared for use in accordance with the present invention by mixing the powder with distilled water to form a dough. The dough is pressed through a die with 3–4 mm circular holes. The extruded dough appears spaghetti-like and is dried and cut to form 5–7 mm length granules. The prepared $CaO_2$ can be loaded into the front of the canister 10 to form bed 34.

The main working compound is prepared by mixing $KO_2$ (or $NaO_2$) and granules of $CaO_2$ in the desired ratio such as 60% $KO_2$ and 40% $CaO_2$ by volume. The mixture is loaded into the canister downstream from the $CaO_2$ (in bed 34) to form bed 32.

The charcoal reagent is prepared by using small dry activated charcoal pieces, generally of irregular shape with average diameters of 4–6 mm and simply pouring distilled water thereover.

The reaction of $CaO_2$ to remove $CO_2$ and add $O_2$ to the gas stream occurs at a higher temperature than the reaction of $KO_2$ or $NaO_2$. For this reason, the contribution of $CaO_2$ to the air revitalizing process is delayed with respect to the contribution of $KO_2$ or $NaO_2$. The use of alkaline-earth metal peroxide along with an alkali metal superoxide (or peroxide with respect to Li) provides the additional benefit of prolonging the useful life of the canister.

Figure 2:
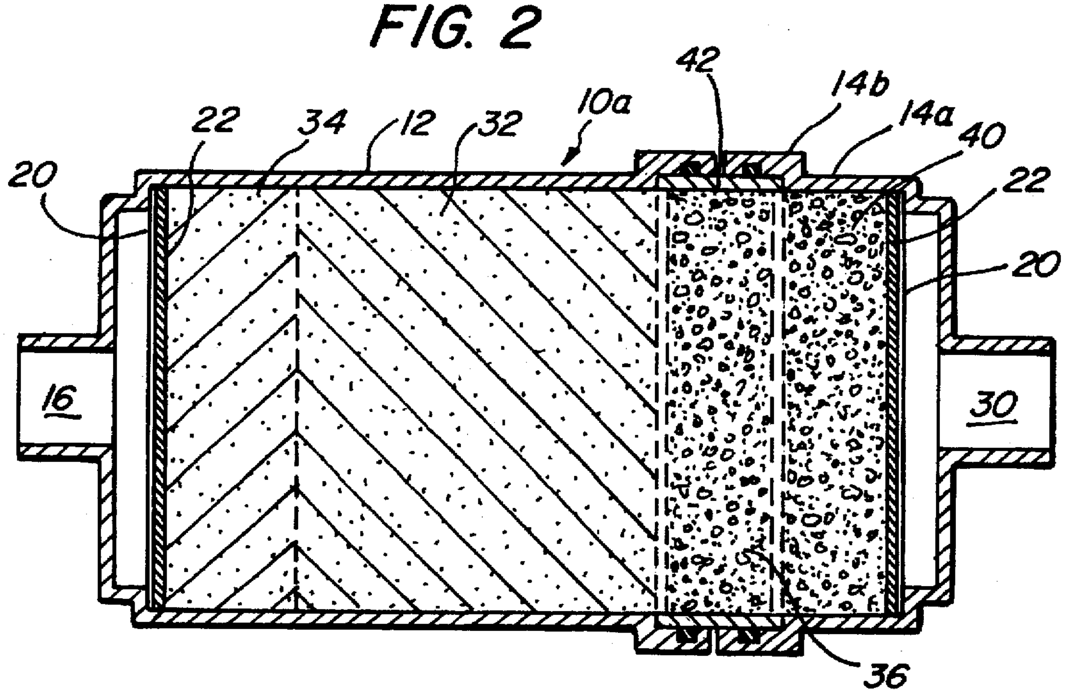
FIG. 2 is a cross-sectional view of another canister containing an additional air revitalizing compound in accordance with the invention.

Another embodiment of a preferred canister 10*a* containing air revitalizing compounds, in accordance with the present invention, is illustrated in FIG. 2. The canister 10*a* contains the same constituents as the canister 10 of FIG. 1 with an additional bed of dry activated charcoal 40 located downstream from the bed 36 of wet activated charcoal. The canister shell includes an intermediate tubular section 42 which receives the wet activated charcoal in bed 36. An outlet section 14*a* holds the bed 40 and includes an annular flange 14*b* which carries another o-ring 44 which is arranged to seal against the outer periphery of the section 42.

Each separate section of the canister may be encapsulated in a suitable impermeable membrane (not shown) for storage purposes. Such membranes may be ruptured and the several sections of the canister 10*a* pushed together immediately prior to use.

The volume of the charcoal in bed 40 may be comparable to the volume of the wet charcoal in bed 36. The dry activated charcoal serves the purpose of decreasing the humidity of the outlet gas or air to about 50–70% versus about 85–100% where only wet activate charcoal is placed downstream from the working compound(s). The reduction in the relative humidity may be helpful in preventing a mask or head enclosure from fogging. It should be noted that the relative humidity of the outlet gas, in the absence of a moisturizing material such as wet charcoal downstream from the working compound, is of the order of only 15–20%.

Figure 3:
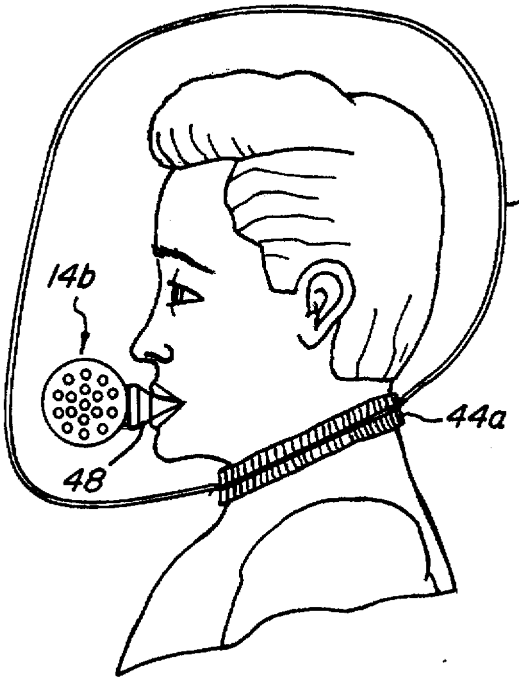
FIGS. 3 and 4 are pictorial views of an emergency closed-circuit breathing system in which a canister incorporating air revitalizing compounds is utilized to maintain the recirculated air suitable for human use for an extended time period.
Figure 4:
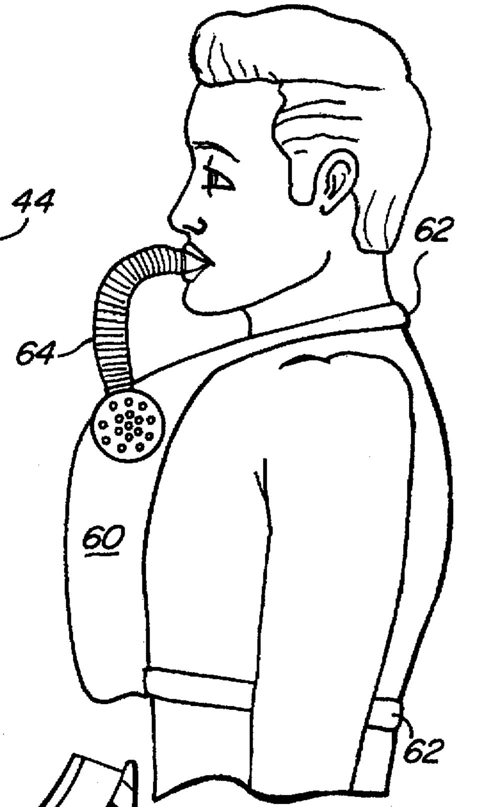
Figure 5:
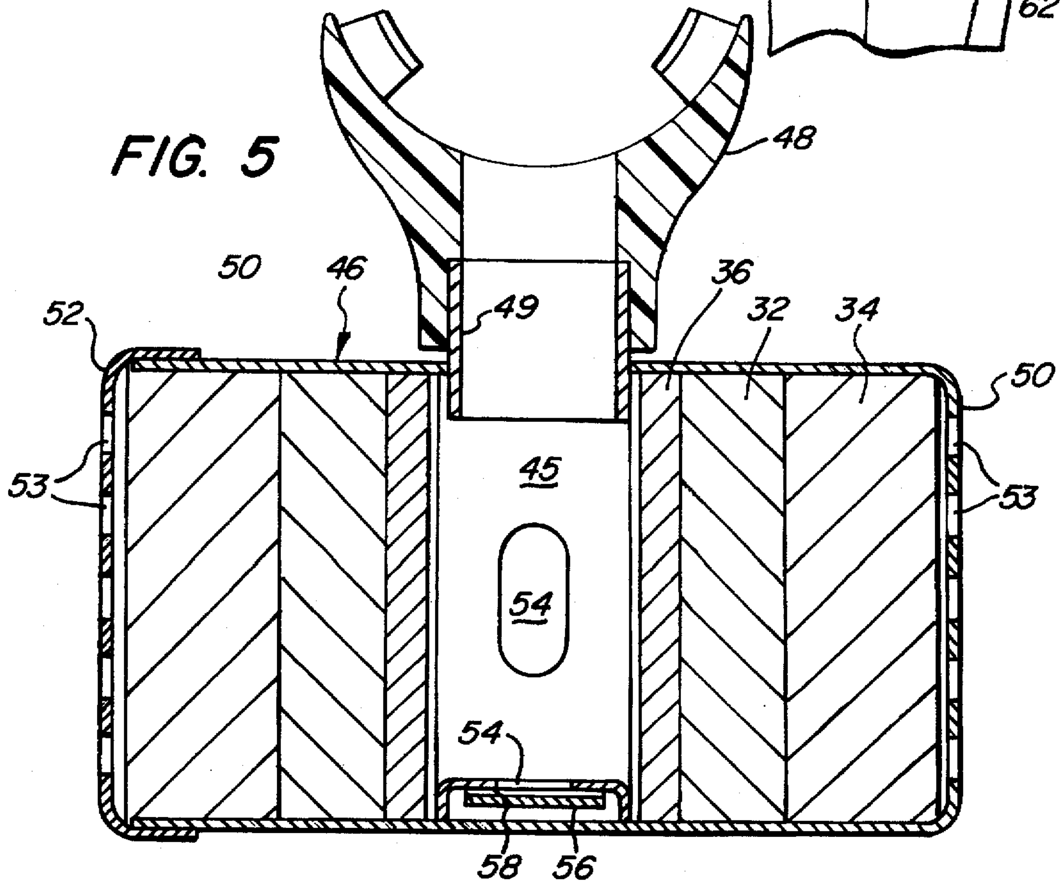
FIG. 5 is a cross-sectional view of a canister and associated mouth piece arrangement suitable for use in the closed-circuit breathing systems of FIGS. 3 and 4.

An emergency closed-circuit breathing system in accordance with the present invention is illustrated in FIGS. 3–5. The system of FIG. 3 includes a rebreather bag 44 of translucent or transparent material made, for example, of a suitable plastic such as FEP film. The bag 44 is arranged to completely envelope the user's head with an elastic neck band 44*a* or other suitable means, for inhibiting or substantially preventing air within the bag from exiting and substantially preventing outside air (which may contain smoke or other harmful materials) from entering the rebreather bag and the user's lungs.

The outlet 45 of a canister 46 containing the air revitalizing material beds 32, 34, and 36, as discussed above, is fitted to a mouthpiece 48 via a tubular section 49, as is illustrated in FIG. 5. It should be noted that the mouthpiece may, if desired, be in the form of a mask and cover the user's nose as well as the mouth. The canister 46 includes a tubular shell 50 capped at each end with a perforated plate 52. The perforations in plates 52 form the inlet ports 53 which allow air from the rebreather bag 44 to enter the canister during the inhalation phase of the user's breathing cycle. Three outlet ports 54 are spaced around the outer periphery of the center section of the shell 50. A flexible band 56 made, for example, of rubber, is secured to the outer periphery of the canister shell and overlaps each of the outlet ports 54. The band 56 in conjunction with the seats 58, surrounding the outlet ports function as a one-way exhalation valve in allowing exhaled air to exit to the interior of the rebreather bag. During the inhalation phase, the ports 54 are closed by the band 56.

FIG. 4 illustrates the use of a rebreather bag 60 which is secured to the user's chest via straps 62. The canister 46 is located within the bag 60. A breathing tube 64 connects the mouthpiece 48 to the tubular fitting 49.

Figure 6:
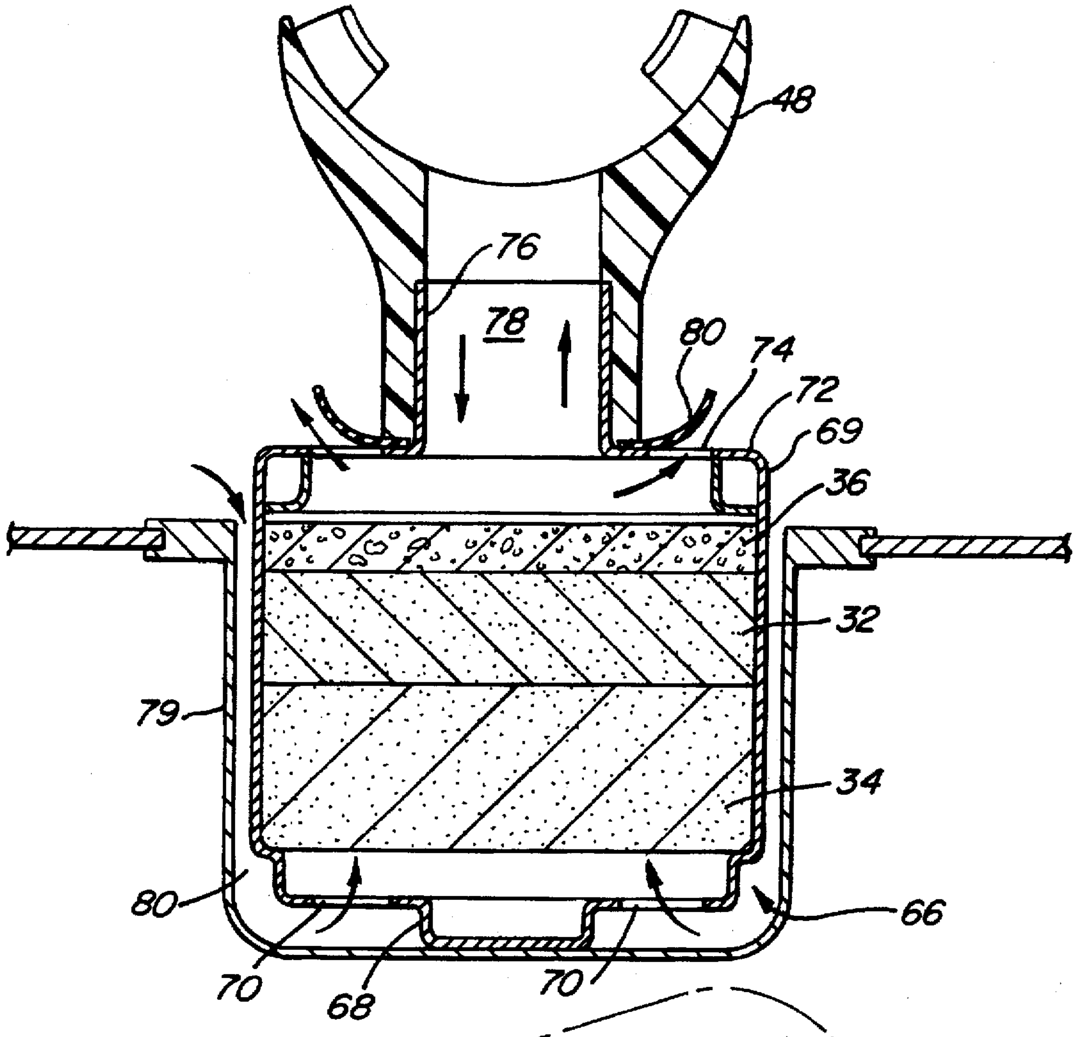
FIG. 6 is a cross-sectional view of another canister and mouth piece arrangement suitable for use in the breathing systems of FIGS. 3 and 4.

Another embodiment of a mouthpiece and canister arrangement is shown in FIG. 6. The canister 66, of FIG. 6, comprises a tubular side wall 68 which terminates at its distal end, in a stepped end wall 69 provided with inlet apertures 70. The proximal end of the canister terminates in an end wall 72 with spaced exhalation openings 74 and a tubular section 76 surrounding an air outlet passageway 78. A cup-shaped flow director 79 directs air from the interior of a rebreather bag, such as those shown in FIGS. 3 and 4 or other suitable container, into the annular passageway 80 between the flow director and the canister and into the inlet openings.

The mouthpiece 48 is mounted over the outlet tube 76. An exhalation valve is formed by a annular flexible band 80 and the seats surrounding the exhalation openings 74. The beds 32, 34, and 36 of the working compounds and the moisture releasing material, discussed with respect to FIG. 1, are placed in the canister 66 to revitalize the exhaled air. The canister 66 may be used with a rebreather bag in the same manner as the canister 46. As is obvious from the drawing, exhaled air passed through the openings 74. During the inhalation phase the exhalation valve is closed by the pressure differential across the openings 74 and air passes through the canister via the annular passageway 80, the inlet aperture 70 and exits into the user's lungs via the outlet 78.

Figure 8:
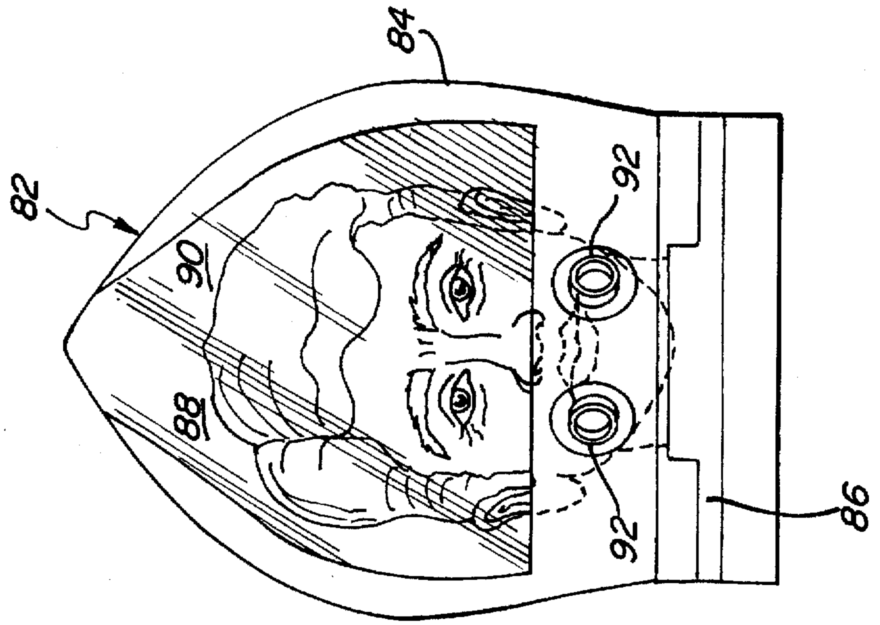
FIG. 8 is a pictorial representation of another embodiment of an emergency closed-circuit breathing system in which a split rebreather bag is positioned inside of a hood covering the user's head.
Figure 9:
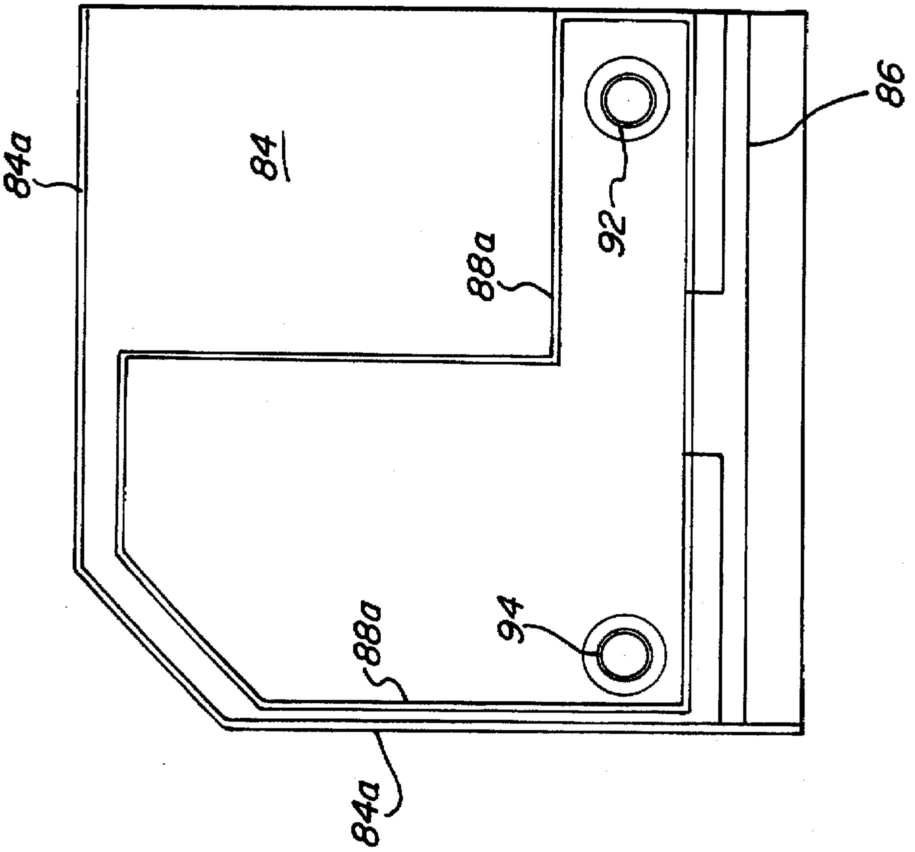
FIG. 9 is a side-elevational view of the hood and rebreather bag arrangement of FIG. 8.

FIGS. 8 and 9 illustrate a three compartment rebreather bag arrangement 82 for substantially preventing the circulating rebreathed air from being contaminated by any external gases which may possibly migrate into an outer compartment or bag through, for example, the type of neck seal discussed with respect to FIG. 3.

The rebreather bag arrangement 82 is shown in FIG. 8 as it would be secured over a user's head and is shown in FIG. 9 in its collapsed planar form. The bag arrangement 82 comprises an outer transparent flexible bag 84 which may be formed by a folded sheet with the free edges 84a thereof sealed to each other and to an elastic neck seal 86.

Left and right inner bags 88 and 90, through which the rebreather air is circulated, are each provided with a mouth piece connector port 92 and a canister connector port 94. The bags 88 and 90 may also be formed out of a plastic sheet and sealed along their respective free edges. The free edge of bag 88 is depicted at 88*a* in FIG. 9. The free edge of the bag 90, although not shown, is identical to the free edge of bag 88.

Figure 10:
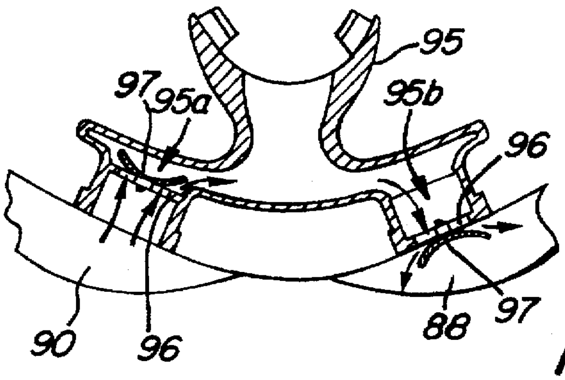
FIG. 10 is a plan view, in cross-section, of a mouth piece and valve device which may be used with the hood/rebreather bag arrangement of FIGS. 8 and 9.

A mouthpiece 95, illustrated in FIG. 10, may be secured to the mouthpiece connector ports 92. The mouthpiece includes inhalation check valves 95*a* and 95*b*, respectively. The check valves are in the form of a perforated plate 96 and a flat flexible (e.g., rubber) disc 97 fastened at its center to the plate with the edges of the disc free to move away from the plate so that air is inhaled from the bag 90 and exhaled into the bag 88.

Figure 11:
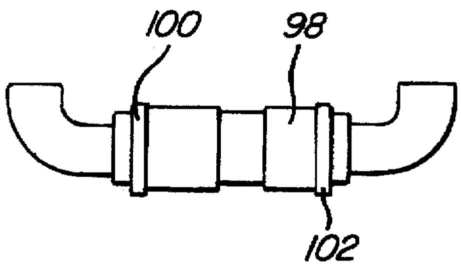
FIG. 11 is a plan view of an air revitalizing canister that may be used with the hood/rebreather bag arrangement of FIGS. 8 and 9.

A canister 98 (FIG. 11) containing the working and moisture-releasing compounds, as discussed in reference to FIG. 1, is connected between the canister connector ports 94 with the inlet 100 thereof arranged to receive the exhaled air from bag 88 and the outlet 102 arranged to provide revitalized air to the bag 90.

Figure 12:
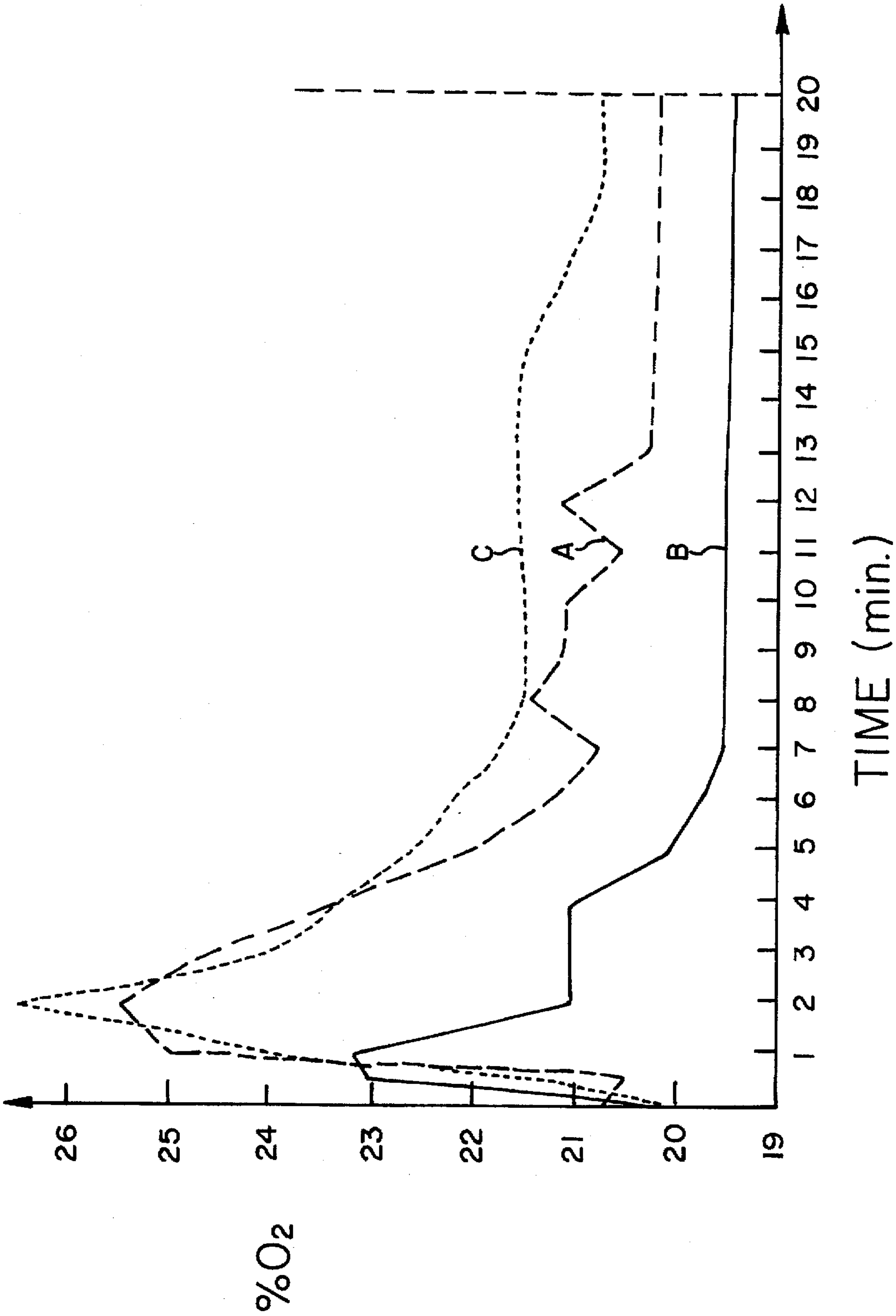
FIG. 12 is a graph illustrating the oxygen replenishment capabilities of certain air revitalizing compounds in a closed-circuit breathing system as a function of time.
Figure 13:
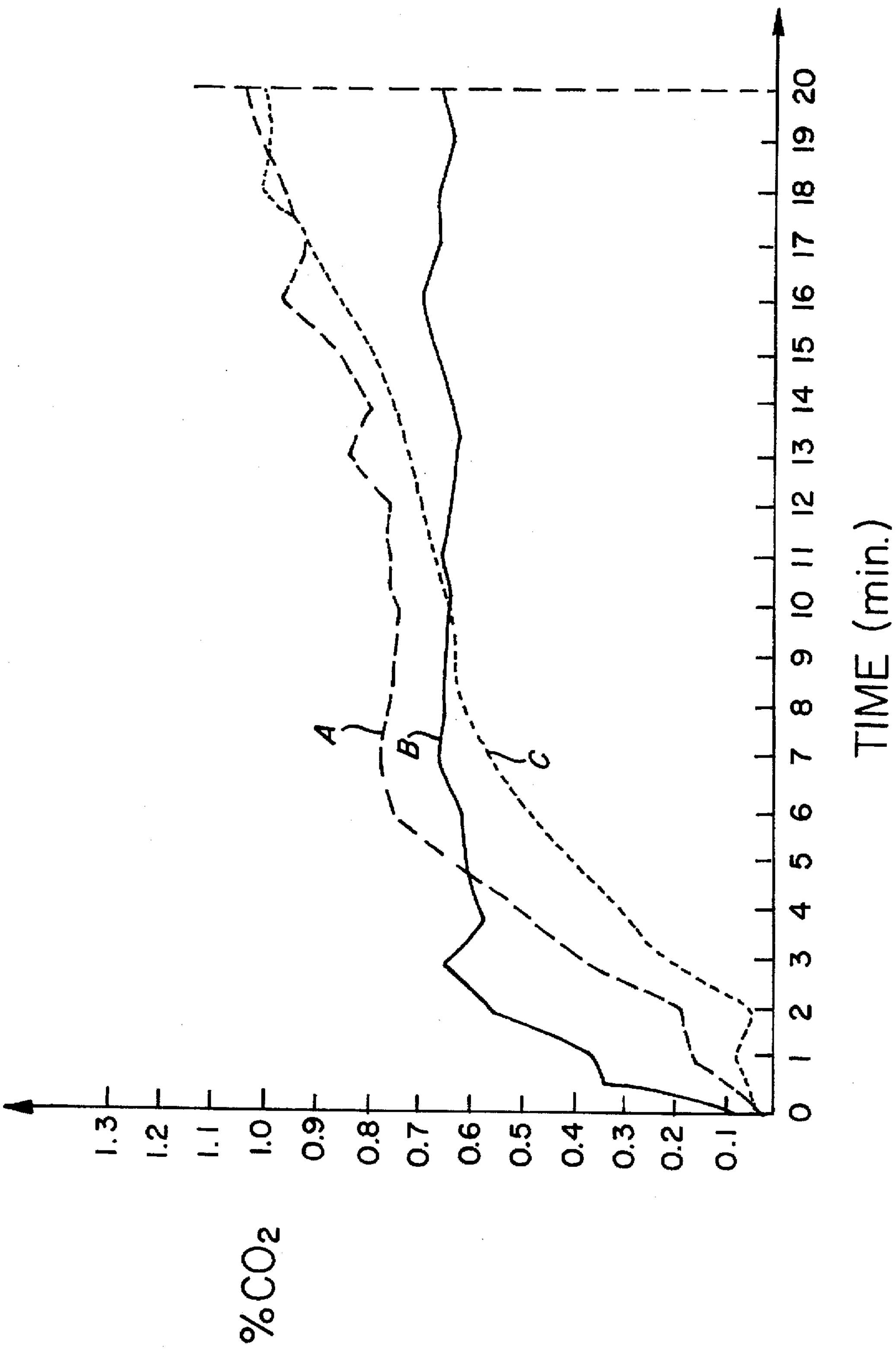
FIG. 13 is a graph illustrating the carbon dioxide absorption capabilities of the compounds utilized in the tests of FIG. 12.
Figure 14:
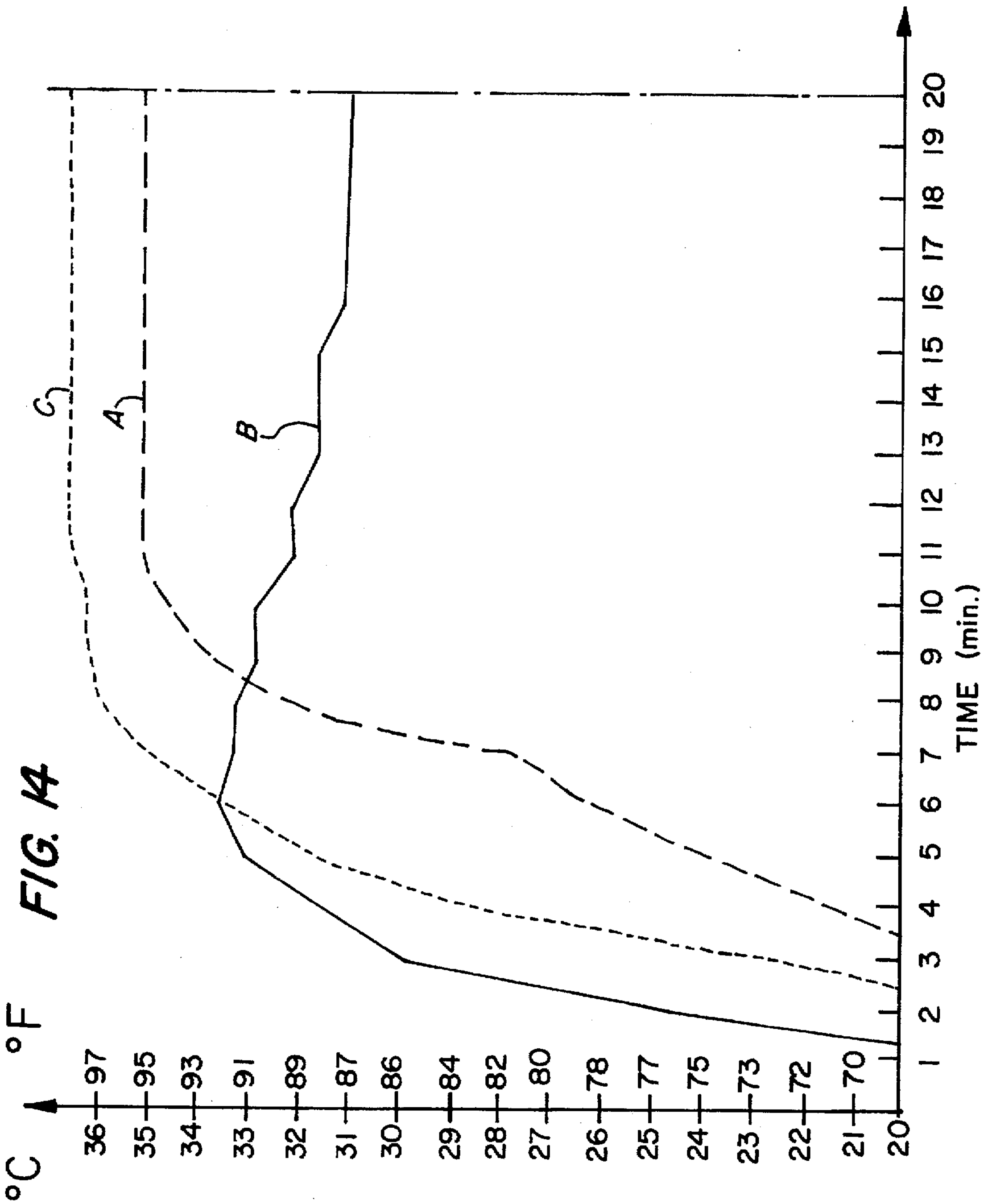
FIG. 14 is a graph illustrating the temperature profile of the outlet air from the canister containing the compounds utilized in the tests of FIGS. 12 and 13.

FIGS. 12, 13, and 14 are graphs showing the $O_2$ content, the $CO_2$ content and the temperature of the air at the outlet of a canister with several varieties of working compounds loaded therein, as a function of time, in an emergency closed-circuit breathing system designed for short term use, i.e., 0–20 or 30 minutes. The parameters were measured during tests in which the user was engaged in various work or exercise related activities. Curves A in the several graphs represent the performance of a canister in which (a) the main working compound bed 36 was loaded with 180 $cm^3$ of mixed $NaO_2$ and $CaO_2$ with the $NaO_2$ comprising 60% of the mixture, (b) the auxiliary working compound bed 34 was loaded with 20 $cm^3$ of $CaO_2$ and (c) the bed 36 was loaded with 125 $cm^3$ of dry activated charcoal soaked with 50 $cm^3$ of distilled water.

The following ingredients were used in the canister in tests B and C:

| | |
|---|---|
| Test B | |
| bed 32 | $NaO_2$ (60%) + $CaO_2$ (40%) – 150 $cm^3$ |
| bed 34 | $CaO_2$ – 50 $cm^3$ |
| bed 36 | 90 $cm^3$ of charcoal + 30 $cm^3$ of water |
| Test C | |
| bed 32 | $NaO_2$ (60%) + $CaO_2$ (40%) – 200 $cm^3$ |
| bed 34 | Empty |
| bed 36 | 90 $cm^3$ of charcoal + 30 $cm^3$ of water |

As is illustrated by FIG. 12, the percent of $O_2$ remained satisfactory for all three variants with the variant B providing only a slightly lower $O_2$ content than ambient air.

As is illustrated in FIG. 13 the percent of $CO_2$, although continuing to rise in tests A and C, was also satisfactory. Also, as is shown in graph 14, the temperature of the revitalized air at the outlet of the canister was acceptable in each test with the variant B loaded canister providing the best overall temperature profile.

Formulations of $KO_2$ and $CaO_2$ were also tested and provided somewhat superior results in such tests as compared with the use of $NaO_2$ and $CaO_2$. The reaction of $KO_2$ with exhaled air generates a little more heat initially, but less heat than the use of $NaO_2$ after a short time.

Figure 15:
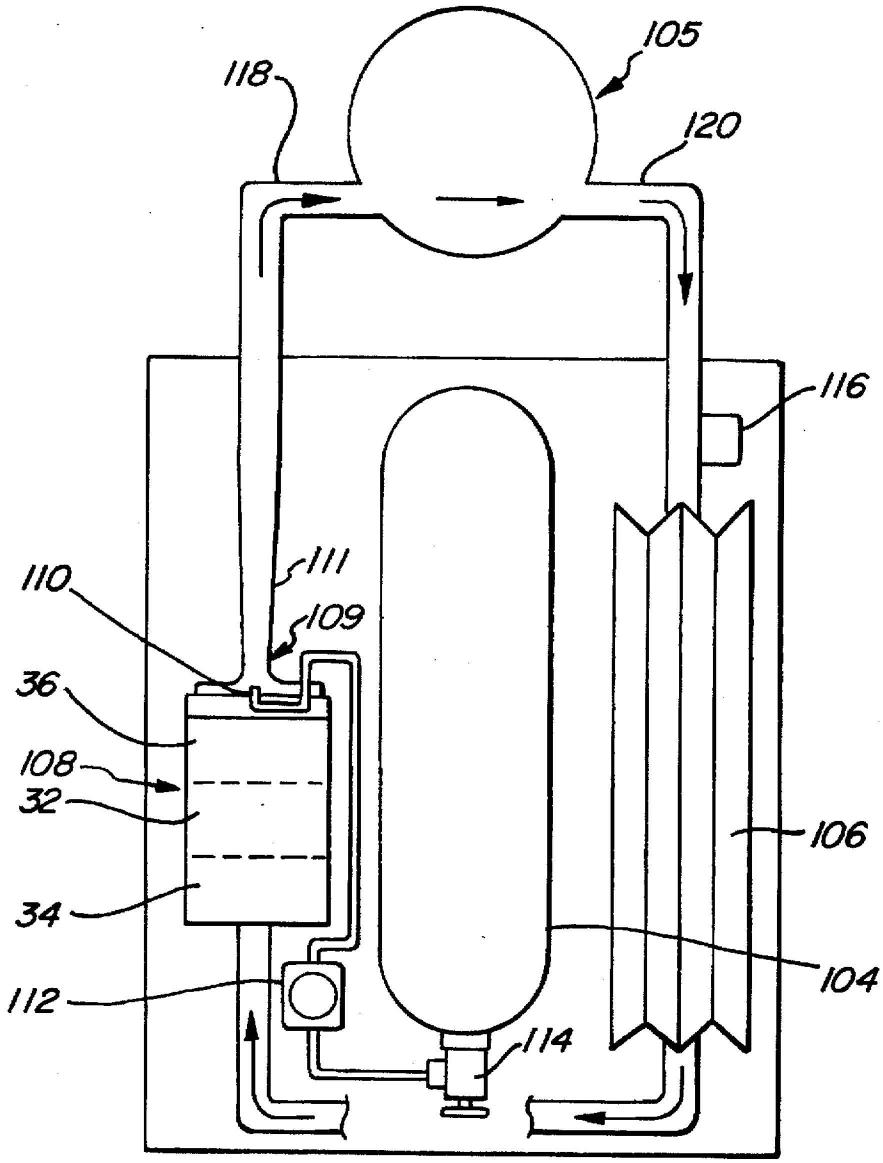
FIG. 15 is a schematic diagram of a semi-closed-circuit breathing system useful for extended periods.

FIG. 15 illustrates a semi-closed-circuit breathing system in which an air cylinder 104 is incorporated into the system to add cool air and provide the energy required to circulate the air stream past the mask and through the rebreather bag and canister. The addition of pressurized air also provides a positive pressure within the user's face mask 105 thereby deterring the ingress of contaminated ambient air into the mask. A similar system utilizing a pressurized source of oxygen or oxygen enriched air and a $CO_2$ absorber is described in U.S. Pat. No. 5,036,841 ("'841 patent"). The use of the air revitalizing compounds of the present invention in such a system eliminates the need and expense to add oxygen or oxygen enriched air to the recirculating gas stream.

In the system shown diagrammatically in FIG. 15 a conventional face mask is connected in a closed loop with a rebreather bag 106 (preferably of the flexible accordion type), a canister 108, containing the air revitalizing compounds discussed above, and an eductor 109 formed by a nozzle 110 and an expansion chamber 111. Air from the pressurized cylinder is supplied to the nozzle 110, at a controlled and adjustable rate such as 5–10 liters/minute ("LPM"), via a pressure regulator 112.

A cylinder valve 114 allows an operator to initiate the flow of air from the cylinder into the recirculating gas stream. A pressure relief valve 116, connected in the line from the mask to the rebreather bag, serves to set the maximum allowed pressure in the system, e.g., at about 2 inches of water. As is illustrated in the figure, exhaled air flows through the rebreather bag 106, then through the canister 108 where the $O_2$ content is increased and the $CO_2$ content decreased. Some exhaled air is also vented to the atmosphere via the pressure relief valve. The wetted activated charcoal, in bed 36, serves to reduce the temperature of the outlet gas and aids in triggering the early production of $O_2$ as discussed above.

The air from the cylinder 104, in flowing through the eductor 110, not only supplies additional air (e.g., preferably about 8 LPM) to the circulating stream, but also provides the energy to circulate the gas through the system at a desired rate (e.g., preferably about 150 LPM). As is explained in the '841 patent, the mask is connected to the junction of the inflow and outflow lines 118 and 120, respectively, so that air is inhaled from and exhaled by the user into the circulating air stream.

It should be noted that where the system, of FIG. 15, is designed for a minimum of two hours of continuous use, it is recommended that the volume of the main and auxiliary compounds in beds 32 and 34 be increased to about 900–1000 $cm^3$ and 150–200 $cm^3$, respectively.

The moisture-releasing compound in bed 36 of the canister 108 may comprise about 300 $cm^3$ of dry charcoal impregnated with about 150 $cm^3$ of water. Where fogging of the face mask is anticipated to be a problem, about 150 $cm^3$ of dry activated charcoal may be placed downstream (in bed 40) from the wetted charcoal.

There has been described a novel method and apparatus for revitalizing exhaled air. While specific examples of closed-circuit and semi-closed-circuit breathing systems have been described it is to be understood that the cartridge of FIGS. 1 and 2 may be used in other systems. Also, modifications of the disclosed systems will be readily apparent to those skilled in the art without involving a departure from the spirit and scope of the present invention as defined in the appended claims.

What is claimed is:

1. A method of treating exhaled air to reduce the $CO_2$ content thereof and to increase the $O_2$ content thereof comprising the steps of:

a) passing the exhaled air through a peroxide and/or superoxide of one or more metals of the groups consisting of the alkali and alkaline-earth metals to reduce the $CO_2$ content and increase the $O_2$ content; and b) adding moisture to the air resulting from the previous step to reduce the temperature thereof.

2. The method of claim 1 wherein one of the metals is potassium.

3. The method of claim 1 wherein one of the metals is sodium.

4. The method of claim 1 wherein the exhaled air is passed through a mixture of $KO_2$ and $CaO_2$.

5. The method of claim 4 wherein the step of adding moisture comprises passing the air through a bed of moistened charcoal.

6. A cartridge for revitalizing exhaled air comprising:

a) a container having an inlet for receiving air having excess $CO_2$ and diminished $O_2$ content and an outlet through which the revitalized air passes;

b) a first bed containing a porous working compound formed of a peroxide and/or superoxide of one or more metals of the alkali and alkaline-metal groups disposed within the container to contact the air as it flows from the inlet to the outlet; and c) a second bed containing a moisture-releasing material disposed in the container downstream from the first bed.

7. The cartridge of claim 6 wherein the container is formed of two sections which are adapted to be separated for storage and snapped together for use, with one section of the container having the inlet opening therein and providing a compartment for the first bed of the working compound, the other section having the outlet opening and providing a compartment for the moisture-releasing material.

8. The cartridge of claim 7 wherein one of the container sections contains a gasket for sealing the sections when snapped together.

9. The cartridge of claim 8 wherein the container sections are cylindrical and further including an impermeable membrane surrounding each separated section, the membranes being rupturable prior to snapping the sections together.

10. The cartridge of claim 6 further including a separate screen individually positioned between the inlet and the first bed and the first bed and the second bed.

11. The cartridge of claim 10 further including at least one dust filter carried by the container for filtering the gas passing through the container.

12. The cartridge of claim 11 wherein one of the peroxides and/or superoxides of the alkali and alkaline-earth metals is $KO_2$.

13. The cartridge of claim 12 wherein one of the peroxides and/or superoxides of the alkali and alkaline-earth metals is $CaO_2$.

14. The cartridge of claim 13 wherein the moisture-releasing material is wetted activated charcoal.

15. The cartridge of claim 6 wherein the first bed contains two compounds mixed together with each compound forming a different peroxide and/or superoxide of one or more metals of the alkali and alkaline-metal groups.

16. The cartridge of claim 15 wherein the first bed contains a mixture of $KO_2$ and $CaO_2$ with the $KO_2$ comprising about 30–70% of the mixture.

17. The cartridge of claim 6 wherein the first bed contains a mixture of $NaO_2$ and $CaO_2$ with the $CaO_2$ comprising about 30–70% of the mixture.

18. The cartridge of claim 16 further including an additional bed of working compound located upstream from the first bed, the additional working compound comprising $CaO_2$.

19. The cartridge of claim 18 wherein the $CaO_2$ is in the form of spaghetti-like granules having an average diameter of about 3–5 mm.

20. The cartridge of claim 6 wherein the moisture-releasing material comprises wetted activated charcoal.

21. The cartridge of claim 17 wherein the moisture-releasing material comprises wetted activated charcoal.

22. The cartridge of claim 21 wherein the percentage of $KO_2$ in the mixture is about 60%.

23. In an apparatus for enhancing the quality of breathable gas the combination comprising:

a) a canister having an gas inlet for receiving gas of excess $CO_2$ and diminished $O_2$, a gas outlet through which the gas of enhanced breathable quality passes and first and second compartments disposed between the inlet and outlet thereof in that order, b) a porous compound of peroxide and/or superoxide of one or more metals of the alkali and alkaline-earth metals disposed within the first compartment to contact the gas as it flows from the inlet to the second compartment and reduce the carbon dioxide and increase the oxygen content thereof; and c) a porous moisturizing material disposed in the second compartment to contact the gas as it flows from the first compartment to the outlet and extract heat therefrom.

24. The invention of claim 23 further including a rebreather reservoir for containing breathable gas and a mouthpiece adapted to be connected to the user's airway, and through which the user's inhaled and exhaled air passes, the canister being connected in series relationship with the canister, mouthpiece and reservoir so that exhaled air passes through the canister before being inhaled by the user.

25. The invention of claim 24 further including a source of pressurized air and a nozzle for injecting air from the pressurized source into the air exhaled by the user.

26. The invention of claim 25 further including:

a mask adapted to be worn by a user and through which breathable gas is inhaled and exhaled by a person wearing the mask, a rebreather reservoir, a conduit connecting the reservoir and canister in series with the mask so that gas can circulate through the reservoir, canister and mask independently of the person's breathing cycle;

a source of pressurized breathable gas;

an eductor having a nozzle positioned in the conduit;

a line connecting the source of pressurized gas to the nozzle of the eductor, whereby the gas flow through the nozzle causes the gas to circulate through the conduit; and a pressure relief valve in the conduit for limiting the maximum pressure therein and for venting excess gas to the atmosphere.

27. The invention of claim 26 wherein the conduit connects the reservoir, canister, eductor and mask in series in that order.

28. The invention of claim 23 further including a three compartment rebreather bag arrangement, the first compartment being adapted to envelope the user's head, the second and third compartments being disposed inside of the first compartment with each of the second and third compartments having a mouthpiece connecting port, and a canister connecting port the canister port of the second and third compartments being connected to the inlet and outlet of the canister, respectively, and further including a mouthpiece connected to the mouthpiece ports of the second and third compartment and check valves for directing exhaled air from mouthpiece into the second compartment and for directing air from the third compartments into the mouthpiece during inhalation.

29. The invention of claim 26 further including an exhalation valve for directing exhaled air into the reservoir.

30. The invention of claim 29 wherein the reservoir is in the form of a flexible bag adapted to be positioned over a user's head.

31. The invention of claim 29 wherein the reservoir is in the form of a bag adapted to be secured to the user's body.

32. A closed circuit breathing system for maintaining the quality of a person's exhaled air at acceptable levels for rebreathing for an extended time period comprising:

a) a rebreather bag adapted to be coupled to the person's airway to provide a closed circulating path for the person's exhaled and inhaled air;

b) a canister disposed within the bag when the bag is coupled to the person's airway, the canister having an inlet port for receiving the exhaled air, an outlet port for providing breathable air for inhalation;

c) a porous working compound and a moisturizing material disposed in the canister in that order between the inlet and outlet ports;

d) the working compound containing peroxides and/or superoxides of one or more metals of the alkali and alkaline-earth metals;

e) one of the inlet and outlet ports of the canister being in fluid communication with the interior of the bag; and f) means including a check valve adapted to selectively connect the person's airway to the other port during one of the exhalation and inhalation modes and to connect the airway to the bag interior during the other mode whereby exhaled air is passed through the canister before being inhaled.

33. The closed circuit breathing system of claim 32 wherein the connecting means is adapted to connect the persons's airway to the outlet port during the inhalation mode and to connect the airway to the bag interior during the exhalation mode.

* * * * *

UNITED STATES PATENT AND TRADEMARK OFFICE
CERTIFICATE OF CORRECTION

PATENT NO. : 5,690,099

DATED : Nov. 25, 1997

INVENTOR(S) : Abramov et al

It is certified that error appears in the above-indentified patent and that said Letters Patent is hereby corrected as shown below:

On the title page, under the "References Cited U.S. Patent Documents" section, please insert the following:

| | | |
|---|---|---|
| 3,390,686 | 7/1968 | Irby, Jr. |
| 3,403,981 | 10/1968 | Lemcke |
| 3,731,678 | 5/1973 | Pyzel |
| 4,020,833 | 5/1977 | Rind |
| 4,112,048 | 9/1978 | Mascher |
| 4,187,843 | 2/1980 | Warncke et al. |
| 4,490,272 | 12/1984 | Malafosse et al. |
| 4,963,327 | 10/1990 | Russell |
| 5,267,558 | 12/1993 | Haertle et al. |

Signed and Sealed this

Fourth Day of May, 1999

Attest:

Q. TODD DICKINSON

*Attesting Officer*

*Acting Commissioner of Patents and Trademarks*